United States Patent [19]

Kerr et al.

[11] 4,081,460

[45] Mar. 28, 1978

[54] PROCESS FOR THE VAPOR PHASE OXIDATION OF BENZENE TO MALEIC ANHYDRIDES

[75] Inventors: Ralph O. Kerr; Gabe W. Strybos, Jr., both of Houston, Tex.

[73] Assignee: Denka Chemical Corporation, Houston, Tex.

[21] Appl. No.: 640,075

[22] Filed: Dec. 12, 1975

Related U.S. Application Data

[63] Continuation-in-part of Ser. No. 563,687, Mar. 31, 1975, abandoned.

[51] Int. Cl.² .......................................... C07D 307/60
[52] U.S. Cl. ................................................ 260/346.75
[58] Field of Search ................... 252/435, 437, 411 R; 260/346.8 A

[56] References Cited

U.S. PATENT DOCUMENTS

| | | | |
|---|---|---|---|
| 2,294,130 | 8/1942 | Porter | 260/346.8 |
| 2,967,185 | 1/1961 | Becker et al. | 260/346.8 |
| 3,296,282 | 1/1967 | Kerr | 260/346.8 |
| 3,838,067 | 9/1974 | Barker | 260/346.8 |
| 3,849,448 | 11/1974 | Crampton et al. | 260/346.8 |

FOREIGN PATENT DOCUMENTS 1,291,354  10/1972  United Kingdom .............. 260/346.8

*Primary Examiner*—W. J. Shine
*Attorney, Agent, or Firm*—Kenneth H. Johnson

[57] ABSTRACT

Molybdenum – vanadium – oxygen oxidation catalyst for producing maleic anhydride from benzene is regenerated and stabilized in situ by the addition of up to 0.0012 gram mole of phosphorus per gram mole of vanadium in the vanadium – molybdenum – oxygen catalyst.

13 Claims, 4 Drawing Figures

YIELD 52 Mol.% MALEIC ANHYDRIDE 640 hrs.
PCl₃ INITIATED

YIELD 60 Mol.% MALEIC ANHYDRIDE 600hrs.
SALT TEMP.

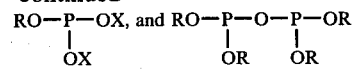

PROCESS FOR THE VAPOR PHASE OXIDATION OF BENZENE TO MALEIC ANHYDRIDES

This application is a continuation-in-part of Ser. No. 563,687 filed Mar. 31, 1975, now abandoned.

BACKGROUND OF THE INVENTION

This invention relates to improvements in the preparation of dicarboxylic acid anhydrides by the vapor phase oxidation of hydrocarbons and more particularly relates to improvements in the process for the catalytic oxidation of hydrocarbons to dicarboxylic anhydrides in the presence of a vanadium — molybdenum — oxygen catalyst.

It has recently been discovered that high yields of dicarboxylic anhydrides may be obtained by oxidizing hydrocarbons in the vapor phase in contact with a vanadium — molybdenum — oxygen catalyst. Although high yields of dicarboxylic anhydrides have been obtained by such processes, it has been found that the yield of product diminishes with time. It is an advantage of this invention to provide a method whereby the useful life of the catalyst bed may be extended by in situ treatment and whereby the high yields may be maintained. It has been found as part of the present invention that one reason for the decrease in yield is the progressive non-selectivity of a portion of the catalyst particles with use and a decrease in the anhydride yield of the process. It is also a feature of this invention to selectively deactivated catalyst particles without impairing the activity of the remaining catalyst particles. This type of phosphorus treatment is readily distinguished from processes such as those disclosed in U.S. Pat. Nos. 3,296,282 and 3,474,041 and British specification 1,291,354 wherein phosphorus is added to replenish phosphorus which is lost during the use of the catalyst and phosphorus added there to actually regenerates the catalyst by replacing lost phosphorus.

SUMMARY OF THE INVENTION

Briefly stated, the present invention is the discovery that vanadium — molybdenum — oxygen catalysts may be treated in situ and stabilized by adding to the catalyst a compound of phosphorus or mixtures thereof. More particularly, volatile, or volatilizable phosphorus compounds or mixtures, are preferably employed.

DRAWINGS

FIGS. 1–4 are graphs showing the deactivation of the original reaction exotherm and relocation thereof deeper in the catalyst bed by the phosphorus treatment of the present invention.

DETAILED DESCRIPTION OF THE INVENTION

Figure 2:
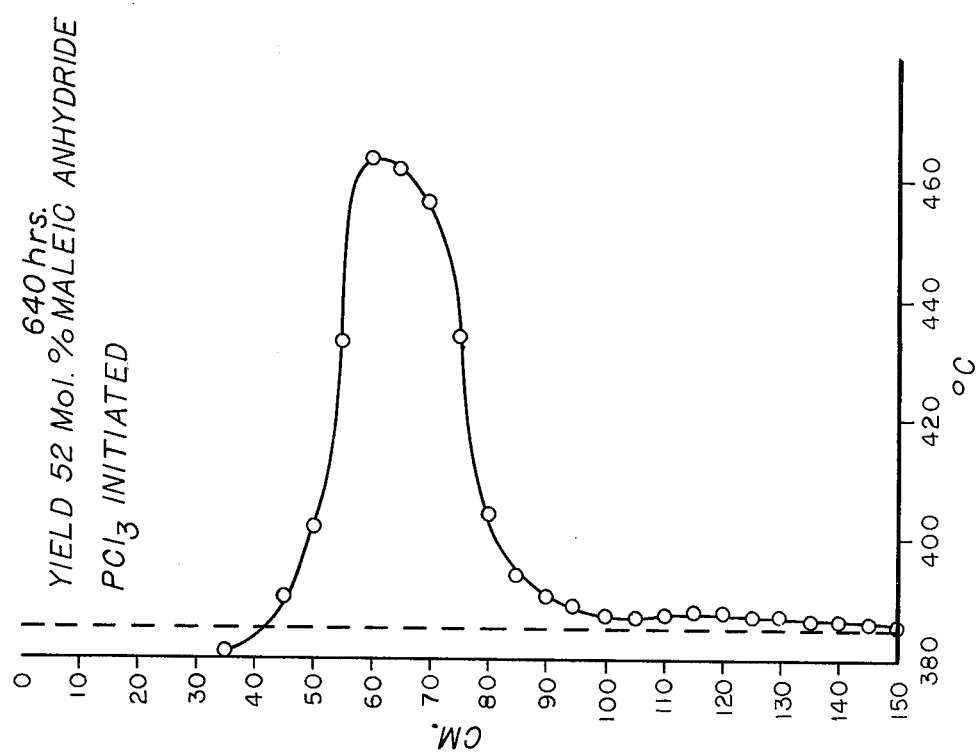

Suitable phosphorus compounds are phosphorus halides of the structure $PX_n'$ wherein $X'$ is Cl, Br, I or F and $n$ is 3 to 5 or an organo-phosphorus compound selected from the group consisting of

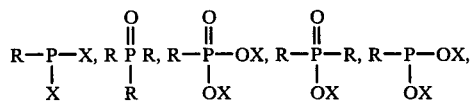

wherein R is phenyl or an alkyl radical of 1 to 6 carbon atoms and X is H or R. Sulphur may be substituted for oxygen in any of these formulas. Suitable compounds are such as the primary, $RPH_2$, secondary, $R_2PH$, and tertiary, $R_3P$, phosphines such as ethyl phosphine; the tertiary phosphine oxides, $R_3PO$, such as tripropyl phosphine oxide; and primary, $RP(O)(OX)_2$, and secondary, $R_2P(O)OX$, phosphonic acids such as benzene phosphonic acid; the esters of the phosphonic acids such as diethyl methane-phosphonate; the phosphonous acids, $RPO_2X_2$, such as benzene - phosphonous acid and the esters thereof such as the monoethyl ester; the phosphonous acids, $R_2POX$, such as diethyl phosphonous acid and the esters thereof such as the monoethyl ester; the primary, $ROP(OX)_2$, secondary, $(RO)_2POX$, and tertiary, $(RO_3)P$, phosphites such as diethyl phosphite, trimethyl phosphite, triethyl phosphite, triisopropyl phosphite, tripropyl phosphite and tributyl phosphite, and the pyrophosphites such as tetraethyl pyrophosphite. Suitable phosphorous compounds are such as phosphorus trichloride, phosphorus trifluoride, phosphorus dichloride monofluoride, phosphorus tribromide, phosphorus dibromide trichloride, phosphorus dibromide trifluoride, phosphorus triiodide, phosphorus pentachloride, the diphosphorus halides, e.g., phosphorus dichloride ($P_2Cl_4$), phosphorus diiodide ($P_2I_4$), the primary, $RPH_2$, secondary, $R_2PH$, and tertiary, $R_3P$, phosphines such as ethyl phosphine; the tertiary phosphine oxides, $R_3PO$, such as tripropyl phosphine oxide; the primary, $RP(O)(OX)_2$, and secondary, $R_2P(O)OX$, phosphonic acids such as benzene phosphonic acid; the esters of the phosphonic acids such as diethyl methane-phosphonate; the phosphonous acids, $RPO_2X_2$, such as benzenephosphonous acid and the esters thereof such as the monoethyl ester; the primary, $ROP(OX)_2$, secondary, $(RO)_2POX$, and tertiary, $(RO_3)P$, phosphites such as diethyl phosphite, trimethyl thiophosphite, triethyl phosphite, triisopropyl phosphite, tripropyl phosphite and tributyl phosphite, and the pyrophosphites such as tetraethyl pyrophosphite. Preferred phosphorus compounds are those wherein the phosphorus has a valence of less than plus five. The phosphorus compounds will suitably have a boiling point of no greater than 250° C and preferably will have a boiling point of no greater than 200° C.

The phosphorus compound may be added up to 0.0012 gram mole per gram mole of vanadium in the vanadium — molybdenum — oxygen catalyst and generally in the range of 0.00004 to 0.0008 gram mole per gram mole of vanadium.

In a preferred embodiment, the phosphorus compound used is preferably one which is volatile or will volatilize under the conditions of addition to the hydrocarbon flow, such as, trimethyl phosphite, phosphorus trichloride, triethyl thiophosphate, phosphorus pentafluoride and phosphorus dichloride monofluoride.

The regeneration process of the present invention may be initiated at any time a decline in the activity of the catalyst is noted, usually by a decline in the yield from the process or an increase in the termperature of the hot spot in the catalyst bed. An increase in the temperature of the hot spot may require reduction in the hydrocarbon throughput, thereby also reducing the unit yield.

The vanadium — molybdenum — oxygen catalysts are well known and have been described and used for the preparation of maleic anhydride in numerous patents, for example, U.S. Pat. Nos. 1,636,857; 2,294,130; 2,674,582; 2,885,409; 2,967,185; 3,074,969; 3,163,613; and 3,211,671.

The vanadium — molybdenum — oxygen catalysts to be reactivated according to the present invention, appear to comprise vanadium, molybdenum and oxygen combined in a complex. Suitable catalysts may have overall atomic ratios of molybdenum to vanadium in the range of 0.05 to 0.95:1. The vanadium — molybdenum — oxygen catalyst may contain various stabilizers and modifiers such as nickel, cobalt, iron, manganese, phosphorus, and alkali and alkaline earth metals, generally in the percents of less than 25 weight percent based on the total weight of vanadium and molybdenum. For example, the vanadium — molybdenum — oxygen catalyst may be modified with 0.002 to 0.1 atom of nickel, 0.0053 to 1.106 atom of cobalt, 0.0072 to 0.30 atom of iron, 0.0003 to 0.12 atom of phosphorus and/or 0.011 to 0.76 atom of lithium, sodium, potassium, calcium or strontium per atom of vanadium. The atomic ratio of oxygen to the remaining components of the catalyst, when the catalyst is in the process of being used to catalyze the oxidation is difficult to determine and is probably not constant due to the competing reactions of oxidation and reduction taking place during the reaction at high temperatures. The overall ratio of oxygen to the combined atoms of vanadium and molybdenum at room temperature would be such as about 4 to 10 atoms of oxygen per the combined atoms of vanadium and molybdenum. At any rate the catalyst is present during the reaction as an oxide of vanadium and molybdenum.

The vanadium — molybdenum — oxygen catalyst may be prepared in a number of ways, as shown in the art. The catalyst may be prepared by precipitating the vanadium and molybdenum compound, either with or without a carrier, from a colloidal dispersion of the ingredients in an inert liquid. The catalyst may also be prepared by dissolving vanadium and molybdenum compounds in a common solvent, such as hot oxalic acid and thereafter depositing the solution on a carrier. In some instances, the catalyst may be deposited as molten metal compounds on a carrier; however, care must be taken not to vaporize off any of the ingredients. The catalyst may also be prepared by heating and mixing anhydrous forms of molybdenum acids with vanadium compounds.

In one particular method of catalyst preparation the desired amount of molybdenum oxide is introduced by dissolving ammonium molybdate in concentrated hydrochloric acid. Then, the desired amount of ammonium vanadate was dissolved in the solution. The other components, if any, are dissolved in the acid solution, for example, cobalt nitrate, nickel nitrate, sodium chloride, trisodium phosphate and the like. The resulting solution of the mixture of compounds is mixed with granules of ceramically bonded, fused porous alumina, and subjected to evaporation, resulting in the deposition of the catalytic materials on the surface in the pores of the support or carrier. The catalyst - carrier is then calcined in the presence of air in a kiln held at a constant temperature of 650°–800° F.

The process of oxidation described herein is applicable generally to processes for the oxidation of hydrocarbons, e.g., having 4 to 8 carbon atoms, to dicarboxylic acids in the presence of vanadium — molybdenum — oxygen catalysts. However, the process is particularly applicable to processes for the preparation of maleic anhydride, from $C_4$ hydrocarbons and benzene, and especially the preparation of maleic anhydride from benzene, terephthalic anhydride from ortho xylene and paraphthalic anhydride from paraxylene. The oxidation of the hydrocarbon to aliphatic dicarboxylic anhydrides may be accomplished by contacting low concentrations of hydrocarbon in oxygen in contact with the vanadium-molybdenum-oxygen catalyst. Air is the most economical source of oxygen, but mixtures of oxygen and diluent gases, such as nitrogen, may also be employed. Air streams enriched with oxygen may also be used. The gaseous feed stream to the reactor normally will contain about 1.1 to about 1.6 1.6 mol percent hydrocarbons based on the total gaseous stream. About 1.25 to about 1.5 mol percent of the hydrocarbon generally gives optimum output of product, although higher and lower concentrations may be utilized. The flow rates of the gaseous stream to the reactor may be varied within fairly wide limits, but a preferred range is at the rate of about 50 to 200 grams of hydrocarbon per liter of catalyst per hour, and generally will be within the range of about 75 to 150 grams of hydrocarbon per liter of catalyst per hour. Residence time of the gas stream will normally be less than about 5 seconds, such as from about 0.01 to less than 2 seconds. The best results have been obtained at residence times of less than 1 second. The flow rates and residence times are calculated at standard conditions of 760 mm. of mercury and at 25° C. The preferred hydrocarbon feed is benzene.

The temperature of reaction for the oxidation of the hydrocarbon to dicarboxylic anhydrides may be varied. The temperature of reaction will depend to some extent upon the size of the reactor, the hydrocarbon concentration and the particular vanadium — molybdenum — oxygen catalyst being employed. A suitable temperature of reaction is from about 340° to about 500° C, as measured at the maximum temperature in the reactor. Better results have been obtained at temperatures from 360° to 475° C. The pressure on the reactor is not generally critical, and the reaction may be conducted at atmospheric, superatmospheric, or below atmospheric pressure.

The oxidation of the hydrocarbons to dicarboxylic anhydrides in the presence of a vanadium — molybdenum — oxygen catalyst may be conducted in a variety of reactors. Fixed bed reactors used for the production of maleic anhydride are quite satisfactory. Multiple tube heat exchanger type reactors have been successfully used. Because the reaction is exothermic, the heat generated must be conducted away from the reactor. Normally, the reactors contain a preheat zone of an inert material.

Catalyst support may be used to give the catalyst physical strength and stability. The carrier may vary in size but generally is from about 2½ mesh to about 10 mesh in the Tyler Standard Screen Size. Useful carriers are such as the inert alumina carriers or the silicon carbides. The amount of the vanadium — molybdenum — oxygen catalysts on the carrier is usually in the range of about 10 to about 35 weight percent of the total weight of complex plus carrier. The final particle size of the catalyst particles will also preferably be about 2½ to about 10 mesh size. The final catalyst particles may be of a variety of shapes, with the preferred shape being the shape of cylinders or spheres or irregular spheres. Inert diluents such as silica may be present in the catalytic surface, but the combined weight of the vanadium, molybdenum and oxygen will preferably be at least 50 weight percent of the catalytic surface.

The phosphorus compounds can be added to the vanadium — molybdenum — oxygen catalysts in a number of different ways. The vanadium — molybdenum — oxygen catalyst will first be used for the oxidation of hydrocarbons to dicarboxylic anhydride for a period of time until the yield of dicarboxylic anhydride diminishes. The phosphorus compound may then be added to reactivate the catalyst. The reactivation step may be accomplished either with or without the flows of hydrocarbon and/or oxygen continued.

A preferred method for the reactivation of the vanadium — molybdenum — oxygen catalyst is by the continuous or intermittent addition of volatile inorganic phosphorus compound to the gaseous stream of hydrocarbons and oxygen — containing gases entering the reactor. By such a technique, the activity of the vanadium — molybdenum — oxygen catalyst is maintained through continuous reactivation or stabilization. An advantage of this procedure is that the production of dicarboxylic anhydride does not have to be interrupted.

Still another method for the addition of the phosphorus compound to the vanadium — molybdenum — oxygen catalyst is by the addition of the phosphorus compound in liquid phase by pouring the phosphorus compound over the catalyst to be reactivated. Reactivation by this technique may suitably be performed at about room temperature if desired.

Thus, the phosphorus compound may be added to the vanadium — molybdenum — oxygen catalyst by a variety of methods such as adding the phosphorus compound as a liquid or gas. Other techniques such as the use of an aerosol to convey the phosphorus compound are also satisfactory. Suspensions or colloidal solutions of the phosphorus compounds may be employed. Solvents for the phosphorus compound may be included. The phosphorus compound may be added such as the hydrocarbon, the oxygen containing gas or via a diluent gas such as nitrogen. The overall temperature range for the addition of the phosphorus compound suitably will be from about 0° to 600° C, depending upon the particular compound selected. However, the preferred temperature of the vanadium — molybdenum — oxygen catalyst at the time of addition of the phosphorus compound will be at least 325° C with still better results being obtained at a catalyst temperature of at least 350° C. The upper limits of the temperature of the catalyst during reactivation will suitably be about 450° or 500° C, or perhaps higher for momentary periods of time. The pressure during the addition may be atmospheric, sub-atmospheric or super-atmospheric. The conditions of concentration, temperature and pressure should be adjusted to permit optimum contact of the phosphorus compound with the vanadium — molybdenum — oxygen catalyst.

As pointed out above, the addition may be either intermittent or continuous. Of course, even if the phosphorus compound is added continuously, it is not necessary that it be added at a constant rate.

Figure 1:
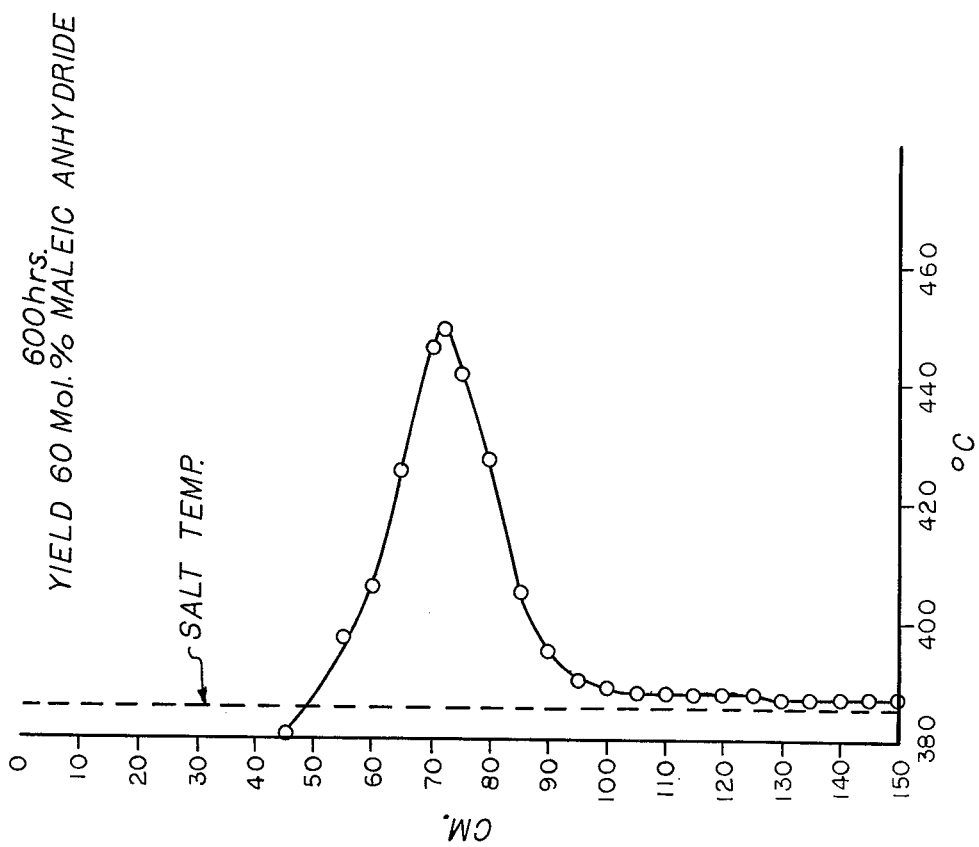

It has been found that by utilizing the process of this invention, the non-selective, catalyst particles are selectively treated. The phosphorus compound selectively deactivates some portions of the catalyst, more specifically, the phosphorus deactivates the non-selective reaction exotherm and causes the reaction exotherm to migrate deeper into the catalyst bed in a beneficial manner. The reaction exotherm of an oxidation is shown in FIG. 1. Note that the major portion of the catalyst bed is substantially unused, however over a period of time that portion of the catalyst bed (fixed bed) wherein the reaction exotherm is located, becomes less selective with a corresponding drop in the yield of the anhydride product, increase in CO and $CO_2$, and increase in the hot spot temperature. Thus, according to the present invention the phosphorus compound is added to deactivate the non-selective reaction exotherm and to allow a new exotherm to occur in the relatively unused portion of the bed, more specifically, that portion of the bed may be characterized as less used. Hence, there will be an improvement obtained over the relatively non-selective reaction exotherm, however, the yield of the process may not again achieve the peak obtained with fresh catalyst. This process may be repeated as long as there is sufficient catalyst bed into which the exotherm may migrate. It should be appreciated that too much of the phosphorus compound passed into the catalyst bed can deactivate the entire bed, thus an appropriate method of obtaining the benefits of the present invention is to add small amounts of phosphorus compound, allow the reaction to stabilize, then to add another small incremental amount and so forth until the original exotherm is deactivated and the relocated exotherm is at an acceptable location.

Another advantage of the invention is that a fixed catalyst bed containing a preheat zone of inert particles may be activated without removing the preheat zone or the catalyst particles from the reactor. The reactivation procedure does not cause the catalyst bed to be plugged.

EXAMPLE 1

Benzene was oxidized to maleic anhydride in a 1.06 inch carbon steel, 12 foot long reactor. The reactor was cooled by a salt bath. A mixture of 1.35 mole percent benzene in air was fed to the reactor. The flow rate was 92.4 grams of benzene per liter of catalyst per hour. The catalyst comprised an oxide of vanadium and molybdenum. The actives were supported on an inert carrier. The catalyst gave a maximum yield of 88.2 weight percent maleic anhydride after 1400 hours at a throughput of 9.06 pounds of benzene per tube per day. The reactor temperature at this time was maintained in the range of 360° to 410° C. After 9200 hours of operation the yield had dropped to 72.9 weight percent maleic anhydride, together with an increased amount of CO and $CO_2$. After 9300 hours of operation, the catalyst was reactivated. To the benzene - air feed stream was added 0.05 liters per minute of trimethyl phosphite and then phosphorus trichloride. A total 2000 ml. each of $(CH_3O)_3P$ and $PCl_3$ was added in this manner over a 2 hour period. After a 2 hour period during which the reaction continued 2 lb. of $MoF_6$ was added over a 0.5 hour period. After b 9600 total hours of operation the yield of maleic anhydride was 80.4 wt. percent, and the percent CO and $CO_2$ had dropped significantly. After 9900 total hours of operation, an additional 2000 ml. of phosphorus trichloride was added in the same manner as the original addition followed by 1 lb. of $MoF_6$ to reactivate the catalyst. After 10200 total hours of operation an additional 1000 ml. of $PCl_3$ was added in the same manner followed by 1 lb. $MoF_6$ to again reactivate the catalyst. After 10600 hours of operation the catalyst was producing a yield of 81.7 weight percent maleic anhydride.

EXAMPLE 2

This example establishes that the phosphorus selectively deactivates a portion of the catalyst bed, which has become non-selective in the reaction and there is no regeneration of the non-selective portion by the phosphorus.

The following data was collected in a laboratory reactor. The reactor employed 300 milliliters of catalyst packed in a 3 foot carbon steel tube, ¾ inch inside diameter, with inert ¼ inch Alundum pellets on top of the catalyst material to a height of ⅓ of the height of the catalyst. The reactor was encased in a 7 percent sodium nitrate-40 percent nitrite-53 percent potassium nitrate eutectic mixture constant temperatures salt bath.

The catalyst employed was a vanadium-molybdenum catalyst of the following composition $V_2O_5 - MoO_3 - Co_2O_3 - NaCl$ of the same general type as that used in Example 1. A mixture of benzene and air was fed to the reactor from the top of the bed in vapor phase.

The flow rate varied between 30 and about 100 g benzene per liter of catalyst per hour ($C_6H_6$g/l/hr), with the major portion of the run being between flow rates of 50 and 80 g $C_6H_6$g/l/hr. The benzene concentration varied from a low of 0.36 percent at start up to a high of 1.12 percent, with the major portion of the run being operated at approximately a 1.0 percent benzene concentration.

After the reactor had been on stream for 200 hours a peak in the mole product of maleic anhydride was obtained, i.e., approximately 72 mole percent MA, at a salt bath temperature of 386° C, hot spot of 401, and air flow of 8.0 l/min and benzene concentration of 1.04. The mole percent of maleic anhydride decreased from that point over the next 400 hours at which point the mole percent of MA in the product stream was about 60 percent. This is represented by FIG. 1. What is shown in the Figures is a representation of the temperature profile in the catalyst bed. The vertical portion of the four graphs of the Figures represents the depth of the catalyst in centimeters. It can be seen that the exotherm of the reaction in FIG. 1 is at approximately 72 centimeters, with the exotherm beginning at approximately 50 centimeters. The salt bath was at 385° C, flow rate of 13.6 l air/min, the concentration of benzene was 0.93 percent, and the conversion was 92 percent.

Figure 3:
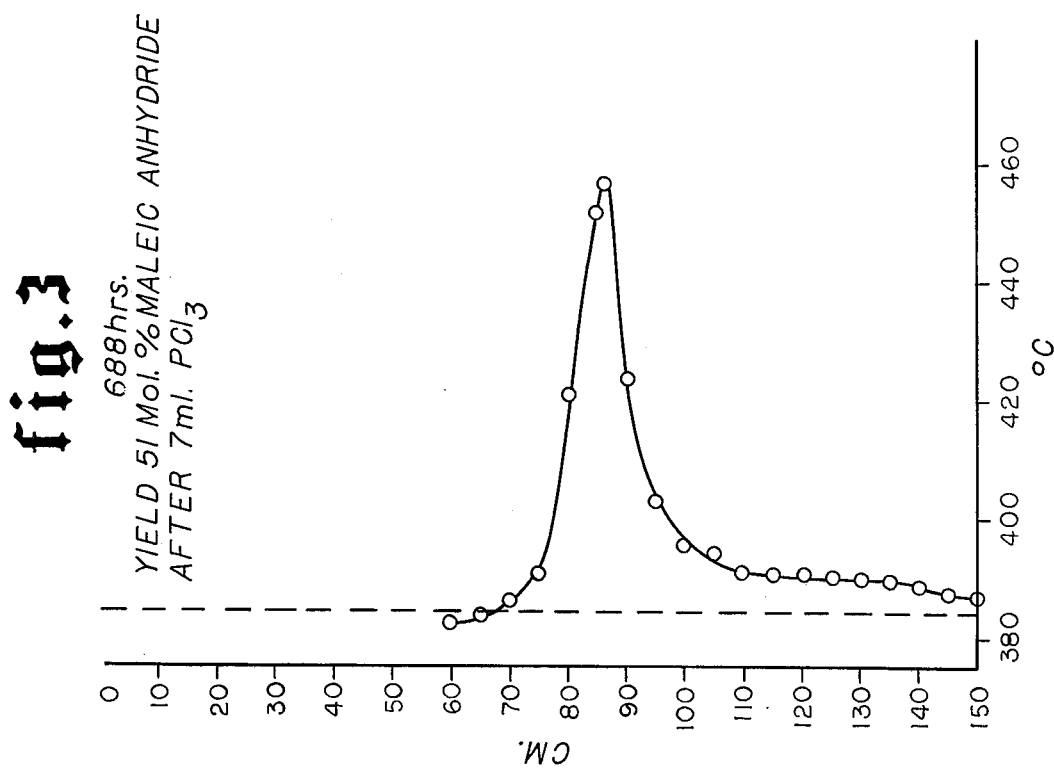

At around 630 hours PCl₃ addition was initiated by bubbling one bubble per minute of nitrogen through PCl₃ into the feedstream to the reactor. The effect of this is demonstrated in FIG. 2. The immediate and initial effect was a dramatic drop in the yield of maleic anhydride from 60 percent to 52 mole percent. Hence, this clearly demonstrates that there is a deactivation, however the full effect of the phosphorus addition is not appreciated at this point since the exotherm of the reaction remains at about the same spot in the catalyst bed. However, after the addition of 7 mls of PCl₃ at approximately 688 hours, which is shown in FIG. 3 it is clearly demonstrated that the initial portion of the bed where the prior reaction, i.e., the exotherm of reaction occurred between 50 and 90 centimeters of catalyst with the peak of the reaction being at approximately 72 cm (FIG. 1) has been almost completely deactivated with the exotherm of reaction now beginning at 75 centimeters of catalyst and extending principally through 105 centimeters with the peak being at 96 centimeters. The yield of maleic anhydride at this time is 51 mole percent.

Figure 4:
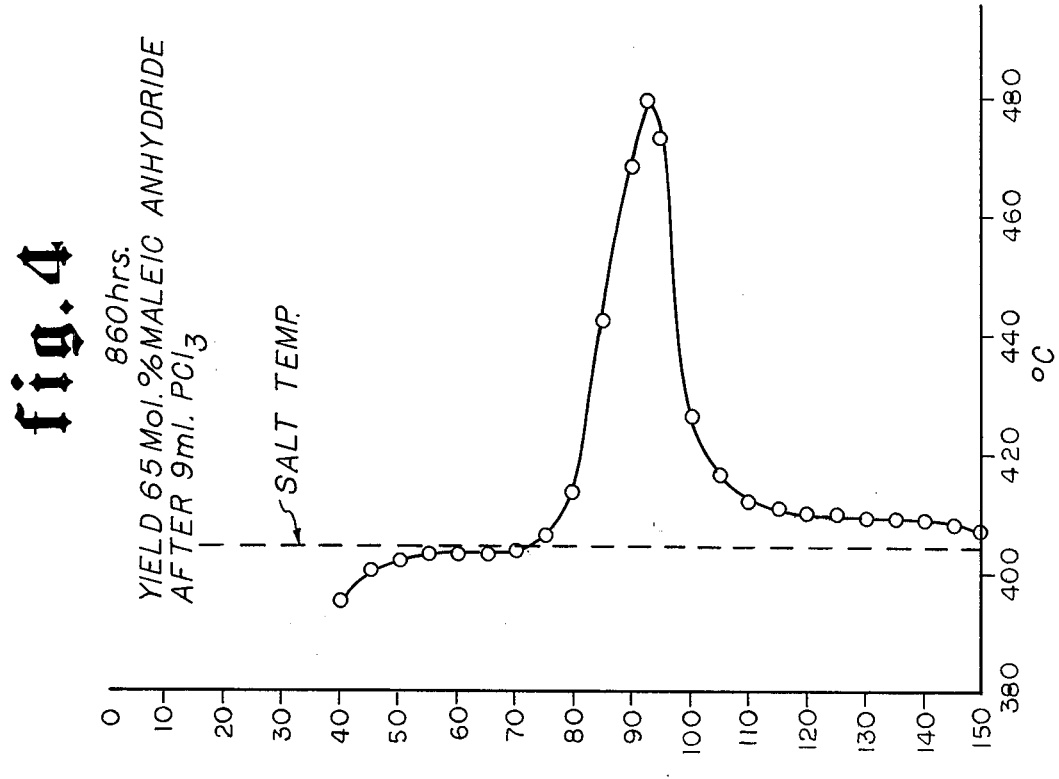

FIG. 4 represents 860 hours on stream after the addition of a total of 9 ml's of PCl₃. The exotherm of reaction now is totally moved so that it is initiated at approximately 80 centimeters of catalyst depth through about 110 with the peak being about 92 centimeters. The exotherm has now been deactivated at the point where it initally occurred, and is in fact moved along in the bed, in this case down in the bed so that catalyst which has not been extensively used is now exposed to the reactants and the yield at this point is 65 mole percent.

Hence, the data clearly shows and establishes that there is no reactivation only deactivation.

The Table provides a summary of the conditions and results corresponding to FIGS. 1–4 and the peak MA yield operation.

TABLE

| Hours | Salt Bath Temp. ° C | Hot Spot ° C | Benzene Flow g/l. cat/hr | Benzene Conc. mole % | Benzene Unreacted mole % | MA Yield mole % | CO+CO₂ mole % |
|---|---|---|---|---|---|---|---|
| 200* | 386 | 401 | 8.0 | 1.04 | 10 | 72 | 13 |
| 600 (FIG. 1) | 385 | 450 | 13.6 | .93 | 10 | 60 | 24 |
| 640 (FIG. 2) | 384 | 458 | 13.6 | .87 | 11 | 52 | 31 |
| 688 (FIG. 3) | 384 | 432 | 13.6 | .92 | 29 | 51 | 15 |
| 860 (FIG. 4) | 404 | 437 | 13.6 | .94 | 7.5 | 65 | 21 |

*Peak Yield of MA

The invention claimed is:

1. In a process for the vapor phase oxidation of benzene to maleic anhydride wherein a stream consisting essentially of said benzene, at about 1.1 to 1.6 mol % of benzene based on the total gaseous stream and a flow rate of 50 to 200 grams of benzene per hour and oxygen, is contacted at a temperature in the range of 340°–500° C with a fixed bed vanadium — molybdenum — oxygen catalyst, having an atomic ratio of molybdenum to vanadium in the range of 0.05 to 0.95:1 and containing less than 25 percent by weight of other components based on the total weight of molybdenum and vanadium, there being an exotherm of reaction in said catalyst bed and wherein said catalyst gradually decreases in activity, the improvement comprising adding to said stream a volatilizable compound of a phosphorus halide or an organo-phosphorus compound selected from the group consisting of

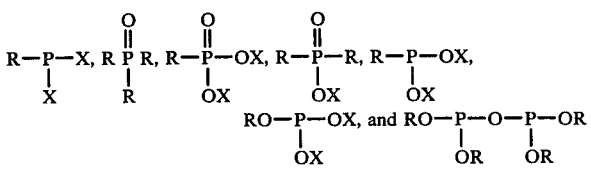

wherein R is phenyl or an alkyl radical of one to 6 carbon atoms and X is H or R, to contact said catalyst in an amount to deactivate only the portion of said catalyst bed containing the exotherm of reaction which was present in said catalyst bed prior to the addition of said phosphorus compound, thereby moving said exotherm down stream into said catalyst bed.

2. The process according to claim 1 wherein said phosphorus compound has a volatilization temperature of 250° C or less.

3. The process according to claim 1 wherein said compound is a phosphorus halide.

4. The process according to claim 1 wherein said compound is an organo-phosphorus compound.

5. The process according to claim 1 wherein up to 0.0012 gram mole of phosphorus compound per gram mole of vanadium in the vanadium — molybdenum — oxygen catalyst is added to the catalyst.

6. The process according to claim 5 wherein from 0.00004 to 0.0008 gram mole of phosphorus compound per gram mole of vanadium is added.

7. The process according to claim 1 wherein said phosphorus compound is added to said catalyst during the vapor phase oxidation of benzene to produce maleic acid anhydride.

8. The process according to claim 1 wherein the phosphorus compound is a phosphorus halide of the structure $PX_n'$ wherein $X'$ is Cl, Br, I or F and $n$ is 3 to 5.

9. The process according to claim 1 wherein said catalyst contains 0.0003 to 0.12 atom of phosphorus.

10. The process according to claim 1 wherein benzene or oxygen are discontinued from said feed during phosphorus compound addition.

11. The process according to claim 10 wherein benzene is discontinued.

12. The process according to claim 10 wherein oxygen is discontinued.

13. The process according to claim 1 wherein benzene and oxygen are discontinued from said feed during the phosphorus compound addition.

* * * * *

UNITED STATES PATENT OFFICE
CERTIFICATE OF CORRECTION

PATENT NO. : 4,081,460
DATED : March 28, 1978
INVENTOR(S) : Ralph O. Kerr & Gabe W. Strybos, Jr.

It is certified that error appears in the above-identified patent and that said Letters Patent are hereby corrected as shown below:

Column 1, lines 65-68 reads "$R\overset{\overset{O}{\|}}{P}R$" but should read -- $R-\overset{\overset{O}{\|}}{\underset{\underset{R}{|}}{P}}-R$ --

Column 4, line 11 reads "in oxygen in contact" but should read -- in oxygen --

Column 4, line 17 reads "1.1 to about 1.6" but should read -- 1.1 to about --

Column 8, lines 56-60 (Claim 1) reads "$R\overset{\overset{O}{\|}}{P}R$" but should read -- $R-\overset{\overset{O}{\|}}{\underset{\underset{R}{|}}{P}}-R$ --

Signed and Sealed this

Eighteenth Day of March 1980

[SEAL]

Attest:

Attesting Officer

SIDNEY A. DIAMOND

Commissioner of Patents and Trademarks